(12) United States Patent
Li et al.

(10) Patent No.: US 11,696,974 B2
(45) Date of Patent: Jul. 11, 2023

(54) METHOD FOR PREPARING A FUNCTIONALLY GRADIENT MATERIAL FOR GUIDED PERIODONTAL HARD AND SOFT TISSUE REGENERATION

(71) Applicant: Sichuan University, Chengdu (CN)

(72) Inventors: Jidong Li, Chengdu (CN); Shu'e Jin, Chengdu (CN); Yubao Li, Chengdu (CN); Yi Zuo, Chengdu (CN); Chen Yuan, Chengdu (CN)

(73) Assignee: Sichuan University, Chengdu (CN)

( * ) Notice: Subject to any disclaimer, the term of this patent is extended or adjusted under 35 U.S.C. 154(b) by 368 days.

(21) Appl. No.: 16/771,221

(22) PCT Filed: Jul. 12, 2019

(86) PCT No.: PCT/CN2019/095661
§ 371 (c)(1),
(2) Date: Jun. 10, 2020

(87) PCT Pub. No.: WO2020/237785
PCT Pub. Date: Dec. 3, 2020

(65) Prior Publication Data
US 2021/0402065 A1    Dec. 30, 2021

(30) Foreign Application Priority Data
May 30, 2019    (CN) .......................... 201910465240.1

(51) Int. Cl.
| | | |
|---|---|---|
| *B29C 41/22* | (2006.01) | |
| *B29C 64/112* | (2017.01) | |
| *B29C 64/118* | (2017.01) | |
| *B29C 70/68* | (2006.01) | |
| *B29C 70/78* | (2006.01) | |
| *B33Y 10/00* | (2015.01) | |
| *D01D 1/02* | (2006.01) | |
| *D01D 7/00* | (2006.01) | |
| *D01D 11/06* | (2006.01) | |
| *D01F 6/70* | (2006.01) | |
| *D01F 6/84* | (2006.01) | |
| *D01F 6/96* | (2006.01) | |
| *A61L 27/56* | (2006.01) | |
| *A61L 27/46* | (2006.01) | |
| *A61L 27/58* | (2006.01) | |
| *D01F 1/10* | (2006.01) | |
| *D01F 6/92* | (2006.01) | |
| *D04H 1/728* | (2012.01) | |
| *D01D 5/00* | (2006.01) | |
| *B32B 37/14* | (2006.01) | |
| *D01F 6/62* | (2006.01) | |
| *C08L 67/04* | (2006.01) | |
| *C08L 89/00* | (2006.01) | |
| *B29K 67/00* | (2006.01) | |

(Continued)

(52) U.S. Cl.
CPC ............... *A61L 27/56* (2013.01); *A61L 27/46* (2013.01); *A61L 27/58* (2013.01); *B32B 37/144* (2013.01); *D01D 5/003* (2013.01); *D01D 5/0038* (2013.01); *D01D 5/0084* (2013.01); *D01F 1/10* (2013.01); *D01F 6/625* (2013.01); *D01F 6/92* (2013.01); *D04H 1/728* (2013.01); *B29K 2005/00* (2013.01); *B29K 2067/04* (2013.01); *B29K 2067/043* (2013.01); *B29K 2067/046* (2013.01); *B29K 2073/00* (2013.01); *B29K 2075/00* (2013.01); *C08L 67/04* (2013.01); *C08L 89/00* (2013.01); *D10B 2331/04* (2013.01); *D10B 2331/041* (2013.01); *D10B 2331/10* (2013.01); *D10B 2331/30* (2013.01)

(58) Field of Classification Search
CPC ..... B29C 41/22; B29C 64/112; B29C 64/118; B29C 70/68; B29C 70/78; B29K 2005/00; B29K 2067/04; B29K 2067/043; B29K 2067/046; B29K 2073/00; B29K 2075/00; B32B 37/144; B33Y 10/00; D01D 1/02; D01D 5/003; D01D 5/0038; D01D 5/0084; D01D 7/00; D01D 11/06; D01F 6/625; D01F 6/70; D01F 6/84; D01F 6/96; D10B 2331/04; D10B 2331/041; D10B 2331/10; D10B 2331/30
USPC .............. 264/211.12, 258, 308, 330, 331.11, 264/331.19, 331.21, 464, 465, 466, 484; 156/244.11, 244.17
See application file for complete search history.

(56) References Cited

U.S. PATENT DOCUMENTS

2021/0077359 A1\*    3/2021    Tayebi ................... A61K 6/831

FOREIGN PATENT DOCUMENTS

| CN | 101584885 A | 11/2009 |
|---|---|---|
| CN | 104474589 A | 4/2015 |

(Continued)

*Primary Examiner* — Leo B Tentoni
(74) *Attorney, Agent, or Firm* — Bayramoglu Law Offices LLC

(57) ABSTRACT

A functionally gradient material for guided periodontal hard and soft tissue regeneration includes a 3D printed scaffold layer and an electrospun fibrous membrane layer. The content of hydroxyapatite in the 3D printed scaffold layer is higher than the content of hydroxyapatite in the electrospun fibrous membrane layer. The pore size of the 3D printed scaffold layer is larger than the pore size of the electrospun fibrous membrane layer. The pore size of the 3D printed scaffold layer is 100-1000 μm, and the fiber diameter of the electrospun fibrous membrane layer is 300-5000 nm. The electrospun fibrous membrane layer is in a random distribution or an oriented arrangement or has a mesh structure. The thickness of the electrospun fibrous membrane layer is 0.08-1 mm.

11 Claims, 4 Drawing Sheets

(51) Int. Cl.
    *B29K 73/00*        (2006.01)
    *B29K 75/00*        (2006.01)

(56)            References Cited

FOREIGN PATENT DOCUMENTS

| | | | | |
|---|---|---|---|---|
| CN | 104874027 A | * | 9/2015 | ............. A61L 27/12 |
| CN | 106110407 A | * | 11/2016 | ........... A61L 31/026 |
| CN | 106110407 A | | 11/2016 | |
| CN | 107213529 A | * | 9/2017 | ........... A61L 31/044 |
| CN | 107320787 A | | 11/2017 | |
| CN | 107823704 A | | 3/2018 | |
| CN | 108914368 A | * | 11/2018 | ............... D01F 1/10 |
| EP | 3311854 A1 | | 4/2018 | |
| KR | 100853816 B1 | | 8/2008 | |
| WO | 2009054609 A1 | | 4/2009 | |
| WO | 2017203331 A1 | | 11/2017 | |

* cited by examiner

METHOD FOR PREPARING A FUNCTIONALLY GRADIENT MATERIAL FOR GUIDED PERIODONTAL HARD AND SOFT TISSUE REGENERATION

CROSS REFERENCE TO THE RELATED APPLICATIONS

This application is the national phase entry of International Application No. PCT/CN2019/095661, filed on Jul. 12, 2019, which is based upon and claims priority to Chinese Patent Application No. 201910465240.1, filed on May 30, 2019, the entire contents of which are incorporated herein by reference.

TECHNICAL FIELD

The present invention belongs to the technical field of biomedical materials, and more particularly, relates to a functionally gradient material for guided periodontal hard and soft tissue regeneration and a preparation method thereof.

BACKGROUND

Guided bone regeneration (GBR) is a procedure that uses barrier membranes to prevent gingival epithelium from migrating onto the root surface, thus creating sufficient space for the reconstruction and regeneration of alveolar bone defects. The guided tissue regeneration technique provides a new strategy for the adjuvant treatment of periodontal diseases and the promotion of bone tissue regeneration. The secondary surgery required for the removal of traditional non-degradable GBR membranes is linked to an increased risk of infection and produces great post-operative pain to patients. Thus, the traditional non-degradable GBR membranes have become obsolete. Collagen-based degradable membranes are mostly derived from mammalian tissues, which poses a potential risk of disease transmission and causes a problem of excessively rapid degradation. Besides, biosynthetic polymer-based degradable membranes have the problem of poor biocompatibility. Moreover, when the GBR membranes are used in clinical procedures, the bone powder should be applied around the implant concurrently to facilitate osseointegration and enhance the repair effect. However, for large-size alveolar bone defects, the implanted bone powder is prone to displacing. In view of the above-mentioned issues, the present invention provides a gradient composite material with integrated functions of guided tissue regeneration membrane and bone filling.

Ideal tissue repair materials can not only simulate the local microenvironment of natural tissues in terms of the compositions and structures, but also have specific biological functions. Electrospinning is a simple, economical and effective method for preparing micro-nano-sized ultrafine fibers, and the fiber structure can well simulate the extracellular matrix structure. The prepared fibrous membranes have the characteristics of large specific surface area and high porosity, and thus are widely used in the field of biomedical materials. Three-dimensional (3D) printing, as a promising printing technology, can produce highly cross-linked structures with high porosity and can print tissue engineering scaffold materials with specific and complex shapes, which has a simple process and can obtain structurally stable and controllable materials.

At present, biopolymer materials commonly used in electrospinning or 3D bioprinting include poly-L-lactide, poly-caprolactone (PCL), poly (lactic-co-glycolic acid), chitosan, polyurethane, etc. Single polymer fibers, however, have low mechanical properties or poor biocompatibility and thus cannot meet the requirements in clinical applications. In recent years, researchers have been devoted to the modification of polymer fibers in order to obtain tissue engineering scaffold materials with excellent performance, and have achieved a series of breakthroughs.

A method for preparing a guided tissue regeneration membrane composed of chitosan and calcium phosphate is disclosed in the prior art. This membrane structure includes a dense layer and a loose porous layer, and has good osteogenic activity, but the chitosan-based biomaterial has the disadvantage of poor mechanical properties. In the prior art, there is also a method for preparing an electrospun fibrous membrane based on hydroxyapatite grafted polylactide/poly (lactic-co-glycolic acid), whereby a novel biodegradable guided tissue regeneration membrane is constructed. This composite membrane exhibits superior mechanical properties, but lacks natural components with good biological activity, e.g., collagen, gelatin, and the like.

Brown et al. prepared a type I collagen modified composite poly (lactic-co-glycolic acid) fiber membrane via electrospinning, but the collagen is derived from a rat tail. Currently, commercial collagen-based guided tissue regeneration membranes (such as Bio-Gide, Bio-Mend, etc.) for clinical use also have the following shortcomings. (1) The membranes are degraded rapidly, causing it hard to maintain space. (2) Collagen is mostly derived from mammalian organs or tissues such as porcine skin, bovine Achilles tendon and the like, which poses a potential risk of disease transmission and may be restricted by issues pertaining to religious practices.

Qingqiang Yao et al. prepared a scaffold material for integrated soft and hard bone repair by performing 3D printing on PCL-grafted amino acids. However, materials for periodontal hard and soft tissue regeneration and repair should also possess a specific mechanical barrier function to prevent gingival epithelial cells from migrating onto the root surface. Therefore, scaffold materials should have a relatively dense structural layer to function as a physical barrier.

SUMMARY

In view of the above-mentioned research status and shortcomings in the prior art, the objective of the present invention is to prepare a functionally gradient material for integrated periodontal hard and soft tissue regeneration and repair by combining the traditional electrospinning technique with the emerging 3D bioprinting technique.

The technical solutions adopted by the present invention are as follows:

A functionally gradient material for guided periodontal hard and soft tissue regeneration includes a 3D printed scaffold layer and an electrospun fibrous membrane layer. The content of hydroxyapatite in the 3D printed scaffold layer is higher than the content of hydroxyapatite in the electrospun fibrous membrane layer. The pore size of the 3D printed scaffold layer is larger than the pore size of the electrospun fibrous membrane layer. The pore size of the 3D printed scaffold layer is 100-1000 µm. The fiber diameter of the electrospun fibrous membrane layer is 300-5000 nm. The structure of the electrospun fibrous membrane layer is in a random distribution or an oriented arrangement or is a mesh structure. The thickness of the electrospun fibrous membrane layer is 0.08-1 mm.

The pore structure changes gradiently, ranging from 300-10000 nm in the fibrous membrane to several hundred micrometers in the scaffold. The material compositions change gradiently as well. The content of apatite in the fibrous membrane is lower, while the content of apatite in the 3D printed scaffold is higher. The content of fish collagen in the fibrous membrane is higher, while the content of fish collagen in the porous scaffold is lower, or even zero. This shows the gradient changes in the pore structure and the composition content between the fibrous membrane and the porous scaffold.

The fish collagen can promote cell adhesion and growth in soft tissues. The scaffold with high apatite content can promote osteogenic differentiation of osteoblasts.

The functionally gradient material can be obtained by compounding the electrospun fibrous membrane with the 3D bioprinted scaffold to form an ABAB structure composed of the fibrous membrane and the 3D bioprinted scaffold. The ABAB structure is repeated alternately in the three-dimensional direction, and the pore structure and porosity are repeated alternately.

The functionally gradient material can be a hard-soft gradient structure formed by the electrospun fibrous membrane wrapping on the surface of the 3D bioprinted scaffold to facilitate the interface bonding between the scaffold material and the host tissue.

The functionally gradient material can be a composite scaffold material formed by shearing the electrospun fibrous membrane into fragments and filling the fragments in the pore structure of the 3D printed scaffold.

The upper layer of the functionally gradient material is composed of the electrospun fibrous membrane with relatively small porosity to effectively prevent gingival epithelial cells and gingival connective tissue cells from migrating onto the root surface. The lower layer of the functionally gradient material is composed of the 3D printed scaffold with relatively large porosity. The functionally gradient material has excellent mechanical properties, a controllable degradation rate, low immunogenicity and good in vivo biological activity, and exhibits gradient changes in both the structure and composition.

A method for preparing the functionally gradient material for the guided periodontal hard and soft tissue regeneration described above includes the following steps:

S1, ultrasonically dispersing nano-hydroxyapatite in a solvent for 1-2 h by a two-step ultrasonic method, then adding fish collagen and poly (lactic-co-glycolic acid) to obtain a mixture, well shaking the mixture for 1.5-3 h, and then ultrasonically dispersing the mixture for 0.5-1 h by the two-step ultrasonic method to obtain a spinning solution;

S2, stirring the spinning solution obtained in step S1 to partially evaporate the solvent to obtain a bio-ink of desired concentration;

S3, preparing an electrospun fibrous membrane layer by using the spinning solution obtained in step S1 via electrospinning; and S4, placing the electrospun fibrous membrane layer obtained in step S3 on a platform of a 3D bioprinter, and printing on the electrospun fibrous membrane layer by the 3D bioprinter using the bio-ink obtained in step S2, to construct the functionally gradient material compounded by the electrospun fibrous membrane layer with the 3D printed scaffold layer.

In the above-mentioned preparation method, alternatively, the 3D printed scaffold layer can be printed by the 3D bioprinter using the bio-ink in advance, and then the electrospun fibrous membrane layer is prepared on the 3D printed scaffold layer by electrospinning, so as to construct the functionally gradient material compounded by the electrospun fibrous membrane layer with the 3D printed scaffold layer.

Poly (lactic-co-glycolic acid) (PLGA) is a biopolymer which is approved by the Food and Drug Administration (FDA) for using in the field of biomedicine. When introduced into PLGA, fish collagen acts as protein molecules and can interact with the molecular chain of the PLGA to form a molecular network structure, thereby improving the mechanical properties of the material. The nano-hydroxyapatite, as the main inorganic constituent of human bone, is introduced into the poly (lactic-co-glycolic acid) to endow the material with significant biological activity and osteogenic induction ability.

The functionally gradient material can be loaded with biological factors or drugs such as dexamethasone, bone morphogenetic proteins (BMP), transforming growth factors (TGF), fibroblast growth factors (FGF), baicalin, and others via the nano-hydroxyapatite, so as to achieve sustained release of the factors or drugs, and endow the material with more functions.

Further, the content of nano-hydroxyapatite in the electrospun fibrous membrane layer is 5-40 wt %, and the content of fish collagen in the electrospun fibrous membrane layer is 1-30 wt %. Preferably, the content of nano-hydroxyapatite in the electrospun fibrous membrane layer is 10-25 wt %, and the content of fish collagen in the electrospun fibrous membrane layer is 5-15 wt %.

Further, the content of nano-hydroxyapatite in the 3D printed scaffold layer is 10-70 wt %.

Further, the hydroxyapatite in step S1 includes short rod-like hydroxyapatite, needle-like hydroxyapatite, microspheric hydroxyapatite and mesoporous hydroxyapatite, and can be replaced with calcium phosphate or calcium silicate.

Further, the poly (lactic-co-glycolic acid) in step S1 can be replaced with one selected from the group consisting of polycaprolactone, polylactic acid, polyurethane and chitosan.

Further, the fish collagen in step S1 is derived from fish skin or fish scale, and the fish is one selected from the group consisting of a cod, a tilapia, a grass carp and a silver carp.

Further, the solvent in step S1 is one selected from the group consisting of trifluoroethanol, hexafluoroisopropanol, dichloromethane, acetone, N, N-dimethylformamide, a mixed solution of the trifluoroethanol and the N, N-dimethylformamide in a volume ratio of 7-9:1-3 and a mixed solution of the acetone and the N, N-dimethylformamide in a volume ratio of 2-4:1.

Further, step S3 specifically includes: collecting randomly distributed fibrous membranes, orientedly arranged fibrous membranes and mesh fibrous membranes by using a flat plate collector, an oriented collector, and a mesh collector, respectively, wherein the electrospinning process parameters include an applied voltage of 7-12 kV, a receiving distance of 12-18 cm, and an injection rate of 0.3-0.6 mL/h; the rotational speed of a roller of the oriented collector is 2000-4000 r/min, and the mesh aperture size of the mesh collector is 400-800 Preferably, the applied voltage is 7-9 kV, the receiving distance is 15 cm, the injection rate is 0.4-0.5 mL/h, the rotational speed of the roller of the oriented collector is 2500-3000 r/min, and the mesh aperture size of the mesh collector is 500-600 μm.

Further, an extruded filament of the 3D printed scaffold layer prepared via 3D bioprinting in step S4 has a diameter of 0.1-0.4 mm. The shape of the scaffold is one selected from the group consisting of a cube, a cylinder, a prism, and other customized shapes required for clinical use.

To sum up, the present invention has the following advantages by employing the above-mentioned technical solutions.

1. In the present invention, the functionally gradient material is compounded by the electrospun fibrous membrane layer with the 3D bioprinted scaffold layer, which can realize the simultaneous repair of periodontal hard and soft tissues. The functionally gradient material exhibits gradient changes in the compositions, pore structures, and orientations of the fibrous membranes and the 3D printed extruded filaments. Thus, the functionally gradient material has more extensive application prospects compared with the fibrous membrane or 3D printed scaffold material alone.

2. The fibrous membrane in the functionally gradient material of the present invention has a relatively dense microporous structure and thus can be used as a mechanical barrier membrane to prevent gingival fibroblasts from migrating onto the root surface and directed to the repair of periodontal soft tissues. The 3D printed scaffold material in the functionally gradient material can be employed to direct alveolar bone regeneration to realize the integrated repair of periodontal hard and soft tissues.

3. The fish collagen used in the present invention is derived from marine organisms, and has the amino acid composition analogous to that of mammals. Moreover, the fish collagen has high biocompatibility, low immunogenicity, high cell affinity and is highly biodegradable. The fish collagen has the amino acid sequence different from that of mammals, and has different immune epitopes, which can avoid the risk of disease transmission without causing issues pertaining to religious practices, cultural sensibilities and ethical problems.

4. A small amount of fish collagen is introduced in the poly (lactic-co-glycolic acid). The formation of molecular network structure due to the hydrogen bonding between the fish collagen molecule and the molecular chain of poly (lactic-co-glycolic acid) significantly improves the mechanical strength of the material. Moreover, the introduction of fish collagen changes the main degradation behavior of poly (lactic-co-glycolic acid) into porous degradation, which significantly accelerates the degradation of the functionally gradient material, and regulates the degradation rate of the material by adjusting the addition amount of fish collagen.

5. In the present invention, the extracellular matrix structure is simulated via fibrous membranes prepared by electrospinning, which is easy to operate by virtue of the mature technology, and has a stable process. The scaffold prepared by 3D bioprinting is highly designable and reproducible, which can meet the personalized needs of patients according to the shape and size of the defect site, thus realizing personalized treatment in clinical use.

BRIEF DESCRIPTION OF THE DRAWINGS

In order to more clearly illustrate the technical solutions of the embodiments of the present invention, the drawings used in the embodiments will be briefly introduced hereinafter. It should be understood that the drawings only show some embodiments of the present invention and thus should not be construed as a limitation on the scope. Those having ordinary skill in the art can also obtain other relevant drawings according to these drawings without creative efforts.

DETAILED DESCRIPTION OF THE EMBODIMENTS

Figure 1:
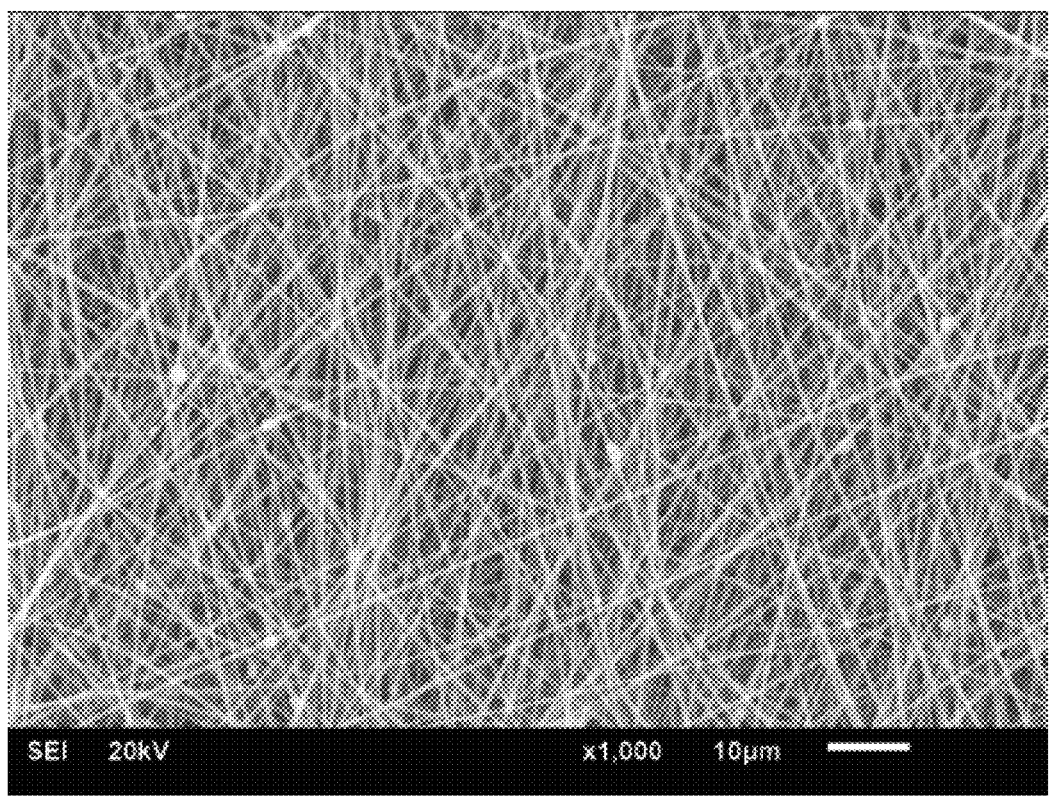
FIG. 1 is an image showing the morphology of the composite nano-hydroxyapatite/fish collagen/poly (lactic-co-glycolic acid) fibrous membrane.

In order to more clearly describe the objectives, technical solutions and advantages of the present invention, hereinafter, the present invention is further described in detail with reference to the drawings and embodiments. It should be understood that the specific embodiments described herein are only intended to illustrate the present invention rather than to limit the present invention, namely, the described embodiments are only a part of the embodiments of the present invention rather than all the embodiments. The components of the embodiments of the present invention described and illustrated in the drawings herein can generally be arranged and designed in various configurations.

Therefore, the following detailed description of the embodiments of the present invention and the drawings are only intended to illustrate the preferred embodiments of the present invention rather than to limit the scope of protection of the present invention. Based on the embodiments of the present invention, all other embodiments obtained by those skilled in the art without creative efforts shall fall within the scope of protection of the present invention.

It should be noted that the terminologies such as "first", "second", and the like are only used to distinguish one entity or operation from another entity or operation without necessarily requiring or implying any such actual relationships or sequences between these entities or operations. Moreover, the terminologies "include", "comprise" or any other variants thereof are intended to cover non-exclusive inclusion, so that a process, method, article or device including a series of elements includes not only those elements, but also includes other elements that are not explicitly listed, or elements inherent to such a process, method, article or device. Without further restrictions, elements defined by the statement "include one . . . " do not exclude the presence of other additional identical elements in the process, method, article or device that includes these elements.

The features and performance of the present invention are further described in detail hereinafter with reference to the embodiments.

Embodiment 1

The preferred embodiment of the present invention provides a method for preparing a functionally gradient material for guided periodontal hard and soft tissue regeneration. The raw materials include: fish collagen purchased from Sangon Biotech (Shanghai) Co., Ltd., hexafluoroisopropanol purchased from Shanghai Aladdin Bio-Chem Co., Ltd., and poly (lactic-co-glycolic acid) purchased from Jinan Daigang Biomaterial Co., Ltd. The specific steps are as follows.

Step 1: 0.06 g of nano-hydroxyapatite is ultrasonically dispersed in 2 mL of hexafluoroisopropanol for 1 h via an ultrasonic cell disruptor.

Step 2: 0.02 g of fish collagen is added into the dispersion solution obtained in step 1 to obtain a mixture, and the mixture is well shaken for 10 min via a thermostatic oscillator;

Step 3: 0.4 g of poly (lactic-co-glycolic acid) is added to the mixed solution obtained in step 2 to obtain a mixture, and the mixture is well shaken for 2 h at 25° C. in the thermostatic oscillator to obtain a spinning solution.

Step 4: The spinning solution obtained in step 3 is ultrasonically dispersed again for 30 min via the ultrasonic cell disruptor.

Step 5: The spinning solution obtained in step 4 is used to prepare the composite nano-hydroxyapatite/fish collagen/poly (lactic-co-glycolic acid) fibrous membrane by an electrospinning machine using a 23 G flat-head needle and a flat plate collector. The electrospinning is performed under parameters including an applied voltage of 8 kV, an injection rate of 0.5 mL/h, and a receiving distance of 16 cm.

Step 6: After being continuously collected for 1 h using a mesh collector in step 5, the fibrous membrane is removed, and then is dried for 3 days in a vacuum drying oven to obtain the electrospun fibrous membrane layer.

Step 7: 0.6 g of nano-hydroxyapatite is ultrasonically pre-dispersed in 10 mL of dichloromethane for 20 min via an ultrasonic cleaner.

Step 8: The dispersion solution obtained in step 7 is ultrasonically dispersed for 30 min by the ultrasonic cell disruptor.

Step 9: 0.2 g of fish collagen is added into the dispersion solution obtained in step 8 to obtain a mixture, and the mixture is well shaken for 20 min via the thermostatic oscillator to obtain a mixed suspension containing the fish collagen homogeneously dispersed in the mixed suspension.

Step 10: 4 g of poly (lactic-co-glycolic acid) is added to the mixed suspension obtained in step 9 to obtain a mixed solution, and the mixed solution is well shaken at 25° C. for 2 h in the thermostatic oscillator.

Step 11: The mixed solution obtained in step 10 is stirred in a fume hood to obtain the bio-ink, wherein the viscosity of the mixed solution is measured to be 40±10 mPa·s.

Step 12: The electrospun fibrous membrane layer obtained in step 6 is placed on the platform of the 3D bioprinter, and the bio-ink obtained in step 11 is used for printing on the composite fibrous membrane by the 3D bioprinter using a conical needle with an inner diameter of 0.16-0.41 mm to obtain the composite nano-hydroxyapatite/fish collagen/poly (lactic-co-glycolic acid) scaffold. The 3D printing is performed under parameters including a scaffold size of 10×10×5 mm$^3$, an extrusion pressure of 5 bar, a needle temperature of 30° C., a receiving platform temperature of 20° C., a needle velocity of 4 mm/s, an initial needle-to-platform distance of 0.208 mm, a layer spacing of 0.208 mm, an initial needle tip-to-platform distance 0.208 mm, and a printing line spacing of 0.3-0.8 mm.

Step 13: The printed scaffold is dried for 3 days in the vacuum drying oven to obtain the functionally gradient material.

Embodiment 2

The preferred embodiment of the present invention provides a method for preparing a functionally gradient material for guided periodontal hard and soft tissue regeneration. The raw materials include: fish collagen purchased from Sangon Biotech (Shanghai) Co., Ltd., hexafluoroisopropanol purchased from Shanghai Aladdin Bio-Chem Co., Ltd., and poly (lactic-co-glycolic acid) purchased from Jinan Daigang Biomaterial Co., Ltd. The specific steps are as follows.

Step 1: 0.06 g of nano-hydroxyapatite is ultrasonically dispersed in 2 mL of hexafluoroisopropanol for 1 h via an ultrasonic cell disruptor.

Step 2: 0.02 g of fish collagen is added into the dispersion solution obtained in step 1 to obtain a mixture, and the mixture is well shaken for 10 min via a thermostatic oscillator.

Step 3: 0.4 g of poly (lactic-co-glycolic acid) is added to the mixed solution obtained in step 2 to obtain a mixture, and the mixture is well shaken for 2 h at 25° C. in the thermostatic oscillator to obtain a spinning solution.

Step 4: The spinning solution obtained in step 3 is ultrasonically dispersed again for 30 min via the ultrasonic cell disruptor.

Step 5: The spinning solution obtained in step 4 is used to prepare the composite nano-hydroxyapatite/fish collagen/poly (lactic-co-glycolic acid) fibrous membrane by an electrospinning machine using a 23 G flat-head needle and a flat plate collector. The electrospinning is performed under parameters including an applied voltage of 8 kV, an injection rate of 0.5 mL/h, and a receiving distance of 16 cm.

Step 6: After being continuously collected for 1 h using a mesh collector in step 5, the fibrous membrane is removed, and then is dried for 3 days in a vacuum drying oven to obtain the electrospun fibrous membrane layer.

Step 7: 0.6 g of nano-hydroxyapatite is ultrasonically pre-dispersed in 10 mL of dichloromethane for 20 min via an ultrasonic cleaner.

Step 8: The dispersion solution obtained in step 7 is ultrasonically dispersed for 30 min by the ultrasonic cell disruptor.

Step 9: 0.2 g of fish collagen is added into the dispersion solution obtained in step 8 to obtain a mixture, and the mixture is well shaken for 20 min via the thermostatic oscillator to obtain a mixed suspension containing the fish collagen homogeneously dispersed in the mixed suspension.

Step 10: 4 g of poly (lactic-co-glycolic acid) is added to the mixed suspension obtained in step 9 for well shaking at 25° C. for 2 h in the thermostatic oscillator.

Step 11: The mixed solution obtained in step 10 is stirred in a fume hood to obtain the bio-ink, wherein the viscosity of the mixed solution is measured to be 40±10 mPa·s.

Step 12: The electrospun fibrous membrane layer obtained in step 6 is placed on the platform of the 3D bioprinter, and the bio-ink obtained in step 11 is used for printing on the composite fibrous membrane by the 3D bioprinter. After the printing on one layer is ended, the printing is paused to place the electrospun fibrous membrane layer obtained in step 6 on the first 3D printed layer. The above-mentioned operation is repeated for more than 10 times to prepare the composite nano-hydroxyapatite/fish collagen/poly (lactic-co-glycolic acid) gradient scaffold material formed by the electrospun fibrous membrane and the 3D printed scaffold alternately. A conical needle with an inner diameter of 0.16-0.41 mm is used. The 3D printing is performed under parameters including a scaffold size of 10×10×5 mm$^3$, an extrusion pressure of 5 bar, a needle temperature of 30° C., a receiving platform temperature of 20° C., a needle velocity of 4 mm/s, an initial needle-to-platform distance of 0.208 mm, a layer spacing of 0.2-0.3 mm, an initial needle tip-to-platform distance 0.208 mm, and a printing line spacing of 0.3-0.8 mm.

Step 13: The printed scaffold is dried for 3 days in the vacuum drying oven to obtain the functionally gradient material.

Experimental Example 1

In the experiment, the steps of preparing a composite nano-hydroxyapatite/fish collagen/poly (lactic-co-glycolic acid) fibrous membrane by electrospinning specifically include:

Step 1: 0.06 g of nano-hydroxyapatite is ultrasonically dispersed in 2 mL of hexafluoroisopropanol for 1 h via an ultrasonic cell disruptor.

Step 2: 0.02 g of fish collagen is added into the dispersion solution obtained in step 1 to obtain a mixture. The mixture is shaken well for 10 min via the thermostatic oscillator.

Step 3: 0.4 g of poly (lactic-co-glycolic acid) is added to the mixed solution obtained in step 2 to obtain a mixture. The mixture is well shaken at 25° C. for 2 h in the thermostatic oscillator to obtain a spinning solution.

Step 4: The spinning solution obtained in step 3 is ultrasonically dispersed again for 30 min by the ultrasonic cell disruptor.

Step 5: The spinning solution obtained in step 4 is used to prepare the composite nano-hydroxyapatite/fish collagen/poly (lactic-co-glycolic acid) fibrous membrane by the electrospinning machine using a flat-head needle with a diameter of 23 G and a flat plate collector. The electrospinning is performed under parameters including an applied voltage of 8 kV, an injection rate of 0.5 mL/h, and a receiving distance of 16 cm;

Step 6: After being continuously collected for 2 h, the fibrous membrane is removed from the collector and dried in a vacuum drying oven for 3 days to fully evaporate the solvent.

Step 7: The nano-hydroxyapatite/fish collagen/poly (lactic-co-glycolic acid) fibrous membrane is prepared by electrospinning.

Figure 2:
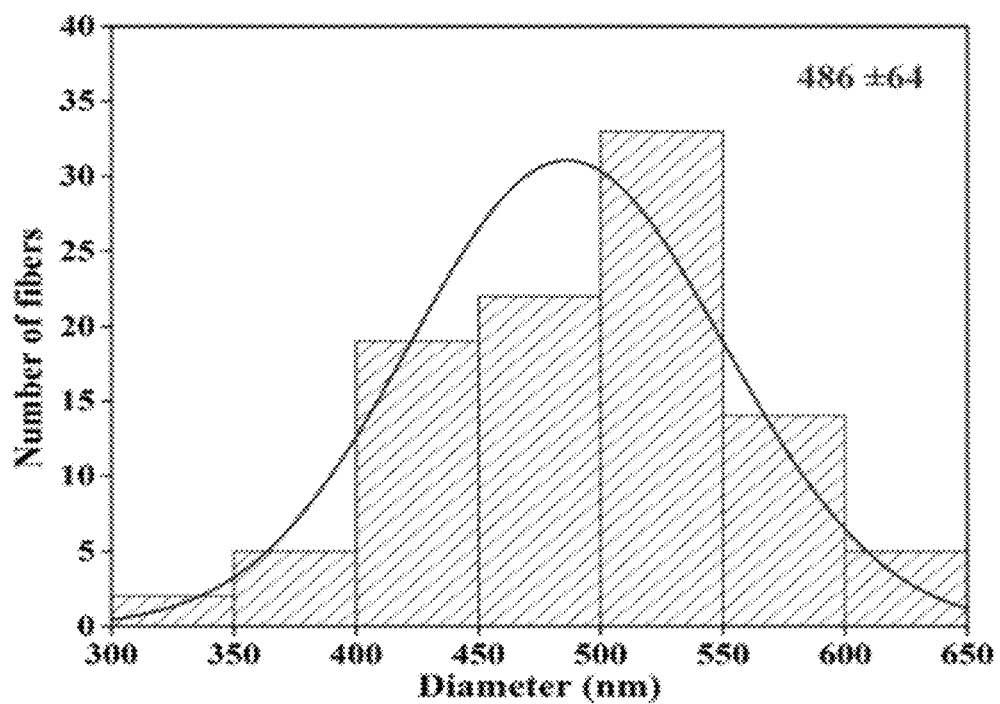
FIG. 2 is a graph showing the fiber diameter distribution of the composite nano-hydroxyapatite/fish collagen/poly (lactic-co-glycolic acid) fibrous membrane.

FIG. 1 shows the observed result of the morphology of the nano-hydroxyapatite/fish collagen/poly (lactic-co-glycolic acid) fibrous membrane via a scanning electron microscope, and no beads are observed on the smooth fibers. FIG. 2 shows the result of a measurement of the diameter distribution, and the average diameter of the fibers is 486±64 nm. The uniform distribution of nano-hydroxyapatite in the fibers is achieved by the two-step ultrasonic method, and the fibers exhibit excellent morphology.

Figure 3:
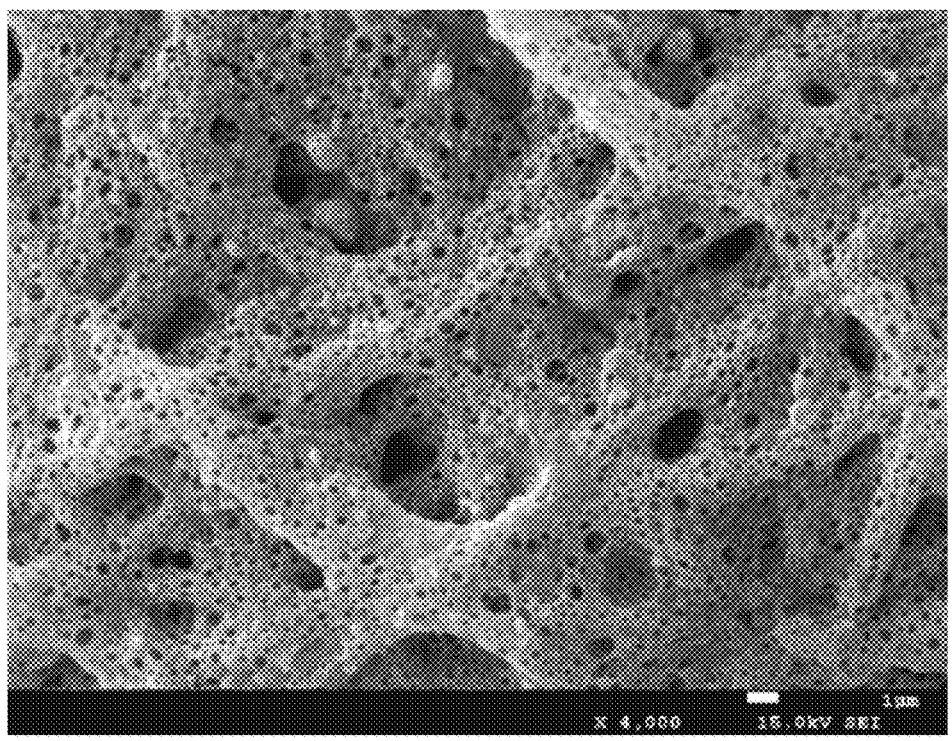
FIG. 3 is an image showing the morphology of the composite nano-hydroxyapatite/fish collagen/poly (lactic-co-glycolic acid) fibrous membrane after being degraded in a phosphate buffer solution for 8 weeks.

FIG. 3 shows the observed result of the morphology of the composite fibrous membrane after 8 weeks of in vitro degradation experiment by the scanning electron microscope. FIG. 3 shows that the introduction of fish collagen changes the main degradation behavior of the fibers. In addition to fiber breakage, fiber swelling and fiber corrosion, porous degradation occurs at the same time, which significantly accelerates the degradation of the fibrous membrane.

Figure 4:
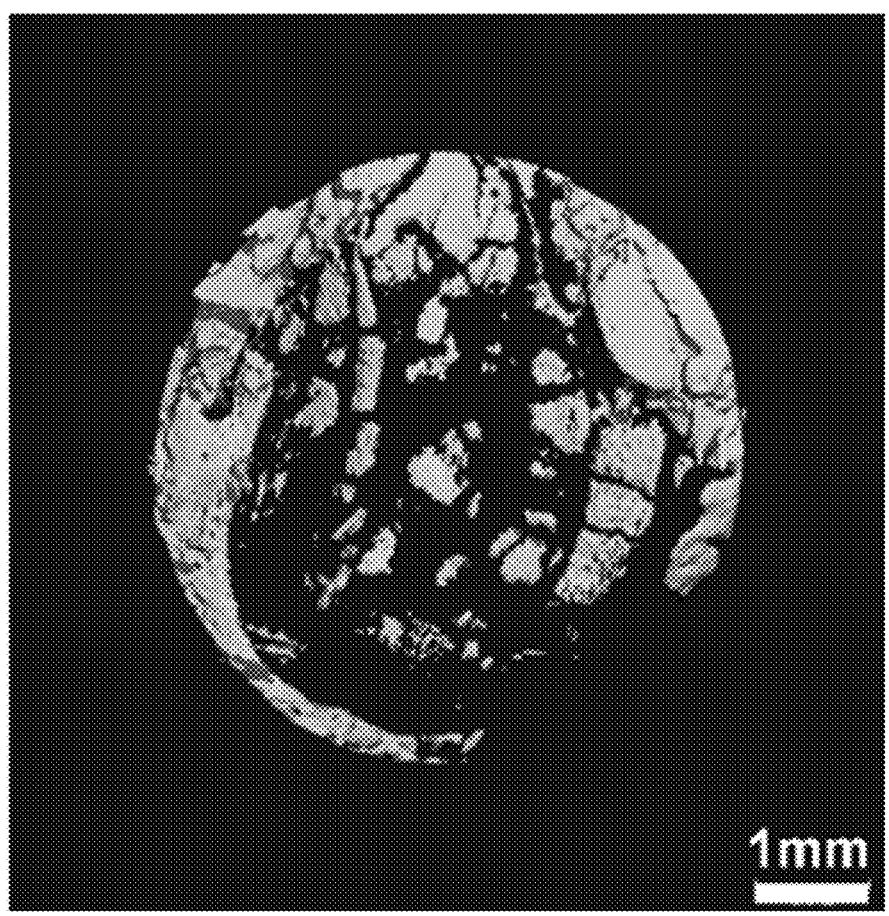
FIG. 4 is an image showing the repair effect in the defect site reconstructed by micro computed tomography (Micro-CT) 4 weeks after the composite nano-hydroxyapatite/fish collagen/poly (lactic-co-glycolic acid) fibrous membrane (PFC5H15) is implanted in a rat model with bilateral cranial defects.

FIG. 4 shows the result of the in vivo bone repair effect of the composite fibrous membrane evaluated by the rat model with bilateral cranial defects. Visibly, new bone tissue is formed in the cranial defect site, indicating that the composite fibrous membrane has promising application prospects in the field of guided tissue regeneration.

Experimental Example 2

In the experiment, the steps of preparing a composite nano-hydroxyapatite/fish collagen/poly (lactic-co-glycolic acid) fibrous membrane by electrospinning specifically include:

Step 1: 0.06 g of nano-hydroxyapatite is ultrasonically dispersed in 2 mL of hexafluoroisopropanol for 1 h via an ultrasonic cell disruptor to obtain a dispersion solution.

Step 2: 0.02 g of fish collagen is added into the dispersion solution obtained in step 1 to obtain a mixture. The mixture is well shaken via a thermostatic oscillator for 10 min.

Step 3: 0.4 g of poly (lactic-co-glycolic acid) is added to the mixed solution obtained in step 2 to obtain a mixture. The mixture is well shaken at 25° C. for 2 h in the thermostatic oscillator to obtain a spinning solution.

Step 4: The spinning solution obtained in step 3 is ultrasonically dispersed again for 30 min by the ultrasonic cell disruptor.

Step 5: The spinning solution obtained in step 4 is used to prepare the composite nano-hydroxyapatite/fish collagen/poly (lactic-co-glycolic acid) fibrous membrane by the electrospinning machine using a 23 G flat-head needle and a flat plate collector. The electrospinning is performed under parameters including an applied voltage of 8 kV, an injection rate of 0.5 mL/h, and a receiving distance of 16 cm.

Step 6: After being continuously collected for 1 h using a mesh collector in step 5, the fibrous membrane is removed, and then is dried for 3 days in a vacuum drying oven.

Figure 5:
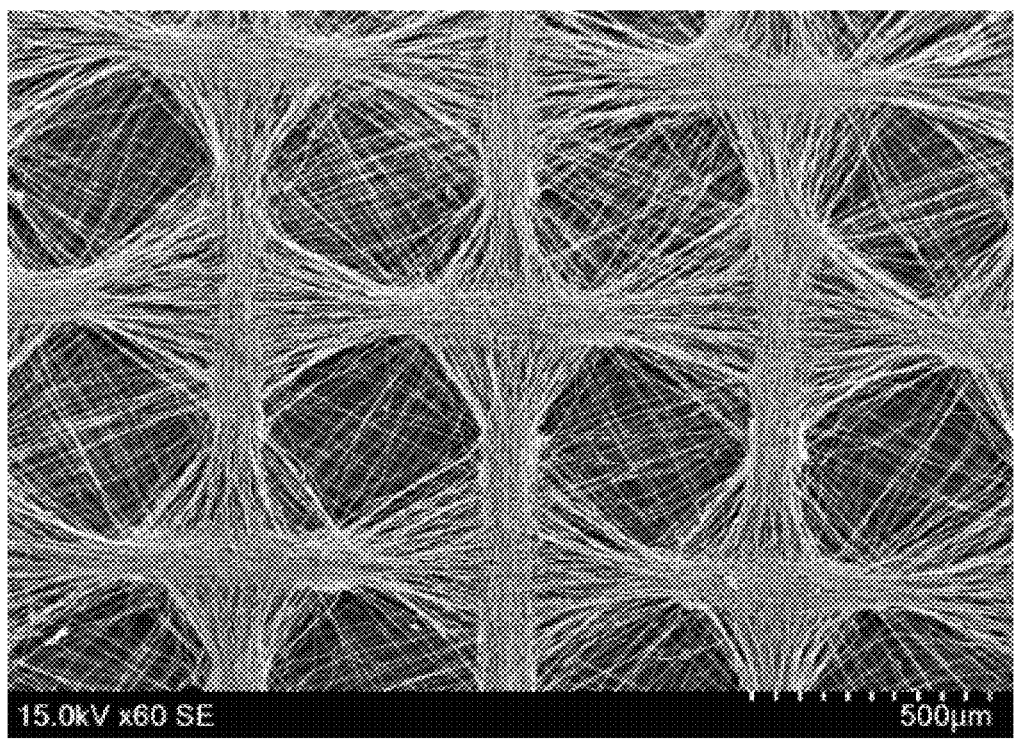
FIG. 5 is an image showing the morphology of the mesh fibrous membrane.

FIG. 5 shows the observed result of the morphology of the mesh fibrous membrane by the scanning electron microscope. The fibrous membrane forms uniformly arranged mesh repeating units with a mesh size of around 500 μm.

Experimental Example 3

Figure 6:
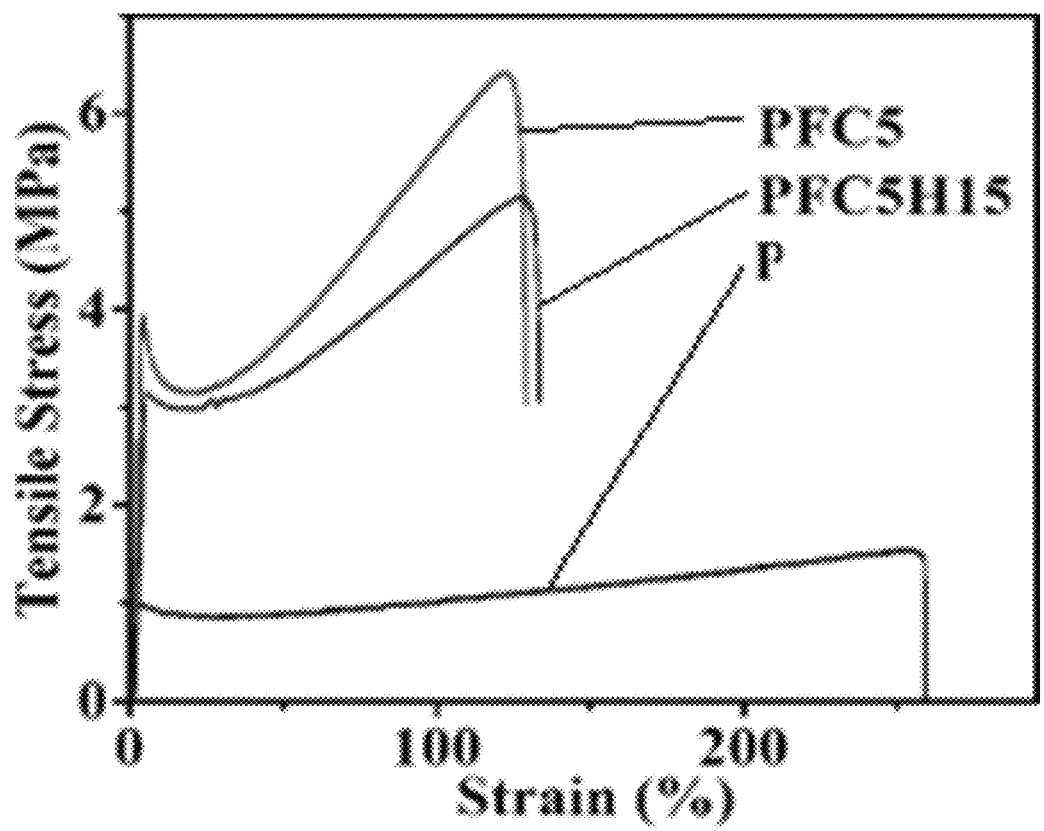
FIG. 6 shows stress-strain curves.
Figure 7:
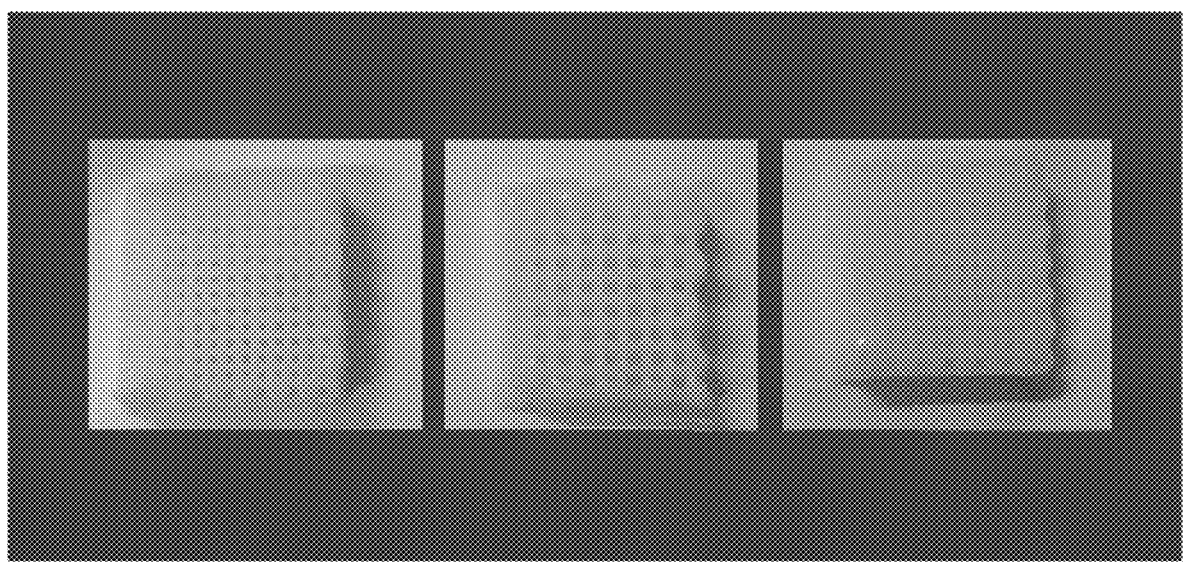
FIG. 7 is an image showing the functionally gradient material compounded by the fibrous membrane with 3D printed scaffolds with different pore structures.

The poly (lactic-co-glycolic acid) fibrous membrane (P), the fish collagen/poly (lactic-co-glycolic acid) fibrous membrane (PFC5) and the composite nano-hydroxyapatite/fish collagen/poly (lactic-co-glycolic acid) fibrous membrane (PFC5H15) are respectively prepared for tensile strength testing. The results thereof are shown in FIG. 6 and Table 1 below. It can be seen that the introduction of fish collagen significantly increases the tensile strength of the fibrous membrane.

TABLE 1

Mechanical properties of the fibrous membranes

| Sample | Tensile strength (Mpa) | Elastic modulus (Mpa) | Elongation at break (%) |
| --- | --- | --- | --- |
| P | 1.5 ± 0.11 | 31.7 ± 4.4 | 232.6 ± 10.9 |
| PFC5 | 6.5 ± 0.13 | 104.8 ± 6.7 | 122.8 ± 10.5 |
| PFC5H15 | 5.2 ± 0.03 | 124.3 ± 22.7 | 127.4 ± 7.5 |

The above-mentioned description is only the preferred embodiments of the present invention and is not intended to limit the present invention. Any modifications, equivalent replacements and improvements made within the spirit and principle of the present invention shall fall within the scope of protection of the present invention.

What is claimed is:

1. A method for preparing a functionally gradient material for a guided periodontal hard and soft tissue regeneration, the functionally gradient material comprising a 3D printed scaffold layer and an electrospun fibrous membrane layer, wherein a content of hydroxyapatite in the 3D printed scaffold layer is higher than a content of hydroxyapatite in the electrospun fibrous membrane layer; a pore size of the 3D printed scaffold layer is larger than a pore size of the electrospun fibrous membrane layer; the pore size of the 3D printed scaffold layer is 100 μm-1000 μm; a fiber diameter of the electrospun fibrous membrane layer is 300 nm-5000 nm; the electrospun fibrous membrane layer is in a random distribution or an oriented arrangement or has a mesh structure; and a thickness of the electrospun fibrous membrane layer is 0.08 mm-1 mm, the method comprising the following steps:

S1, ultrasonically dispersing the hydroxyapatite in a solvent for 1 h-2 h to obtain a dispersion solution, then adding fish collagen and poly (lactic-co-glycolic acid) to the dispersion solution to obtain a mixture, shaking well the mixture for 1.5 h-3 h, and then ultrasonically dispersing the mixture for 0.5 h-1 h to obtain a spinning solution;

S2, stirring the spinning solution obtained in step S1 to evaporate the solvent to obtain a bio-ink;

S3, preparing the electrospun fibrous membrane layer by using the spinning solution obtained in step S1 via an electrospinning; and S4, placing the electrospun fibrous membrane layer obtained in step S3 on a platform of a 3D bioprinter, and printing on the electrospun fibrous membrane layer by the 3D bioprinter using the bio-ink obtained in step S2 to construct the functionally gradient material compounded by the electrospun fibrous membrane layer with the 3D printed scaffold layer.

2. The method for preparing the functionally gradient material for the guided periodontal hard and soft tissue regeneration according to claim 1, wherein, the content of the hydroxyapatite in the electrospun fibrous membrane layer is 5 wt %-40 wt %, and a content of the fish collagen in the electrospun fibrous membrane layer is 1 wt %-30 wt %.

3. The method for preparing the functionally gradient material for the guided periodontal hard and soft tissue regeneration according to claim 1, wherein, the content of the hydroxyapatite in the 3D printed scaffold layer is 10 wt %-70 wt %.

4. The method for preparing the functionally gradient material for the guided periodontal hard and soft tissue regeneration according to claim 1, wherein, the hydroxyapatite in step S1 comprises short rod-shaped hydroxyapatite, needle-shaped hydroxyapatite, microspheric hydroxyapatite, and mesoporous hydroxyapatite.

5. The method for preparing the functionally gradient material for the guided periodontal hard and soft tissue regeneration according to claim 1, wherein, the poly (lactic-co-glycolic acid) in step S1 is replaced with one selected from the group consisting of polycaprolactone, polylactic acid, polyurethane, and chitosan.

6. The method for preparing the functionally gradient material for the guided periodontal hard and soft tissue regeneration according to claim 1, wherein, the fish collagen in step S1 is derived from a fish skin or a fish scale of a fish, and the fish is one selected from the group consisting of a cod, a tilapia, a grass carp and a silver carp.

7. The method for preparing the functionally gradient material for the guided periodontal hard and soft tissue regeneration according to claim 1, wherein, the solvent in step S1 is one selected from the group consisting of trifluoroethanol, hexafluoroisopropanol, dichloromethane, acetone, N, N-dimethylformamide, a mixed solution of the trifluoroethanol and the N, N-dimethylformamide in a volume ratio of 7-9:1-3, and a mixed solution of the acetone and the N, N-dimethylformamide in a volume ratio of 2-4:1.

8. The method for preparing the functionally gradient material for the guided periodontal hard and soft tissue regeneration according to claim 1, wherein, step S3 specifically comprises: collecting randomly distributed fibrous membranes, orientedly arranged fibrous membranes and mesh fibrous membranes by using a flat plate collector, an oriented collector and a mesh collector, respectively, and the electrospinning is performed under process parameters comprising an applied voltage of 7 kV-12 kV, a receiving distance of 12-18 cm and an injection rate of 0.3 mL/h-0.6 mL/h; wherein a rotational speed of a roller of the oriented collector is 2000 r/min-4000 r/min, and a mesh aperture size of the mesh collector is 400 μm-800 μm.

9. The method for preparing the functionally gradient material for the guided periodontal hard and soft tissue regeneration according to claim 1, wherein, an extruded filament of the 3D printed scaffold layer in step S4 has a diameter of 0.1 mm-0.4 mm.

10. The method for preparing the functionally gradient material for the guided periodontal hard and soft tissue regeneration according to claim 1, wherein, the hydroxyapatite is replaced with calcium phosphate or calcium silicate.

11. A method for preparing a functionally gradient material for a guided periodontal hard and soft tissue regeneration, the functionally gradient material comprising a 3D printed scaffold layer and an electrospun fibrous membrane layer, wherein a content of hydroxyapatite in the 3D printed scaffold layer is higher than a content of hydroxyapatite in the electrospun fibrous membrane layer; a pore size of the 3D printed scaffold layer is larger than a pore size of the electrospun fibrous membrane layer; the pore size of the 3D printed scaffold layer is 100 μm-1000 μm; a fiber diameter of the electrospun fibrous membrane layer is 300 nm-5000 nm; the electrospun fibrous membrane layer is in a random distribution or an oriented arrangement or has a mesh structure; and a thickness of the electrospun fibrous membrane layer is 0.08 mm-1 mm, the method comprising the following steps:

S1, ultrasonically dispersing the hydroxyapatite in a solvent for 1 h-2 h to obtain a dispersion solution, then adding fish collagen and a reagent to the dispersion solution to obtain a mixture, shaking well the mixture for 1.5 h-3 h, and then ultrasonically dispersing the mixture for 0.5 h-1 h to obtain a spinning solution, wherein the reagent is selected from the group consisting of polycaprolactone, polylactic acid, polyurethane, and chitosan;

S2, stirring the spinning solution obtained in step S1 to evaporate the solvent to obtain a bio-ink;

S3, preparing the electrospun fibrous membrane layer by using the spinning solution obtained in step S1 via an electrospinning; and S4, placing the electrospun fibrous membrane layer obtained in step S3 on a platform of a 3D bioprinter, and printing on the electrospun fibrous membrane layer by the 3D bioprinter using the bio-ink obtained in step S2 to construct the functionally gradient material compounded by the electrospun fibrous membrane layer with the 3D printed scaffold layer.

* * * * *